(12) United States Patent
Angheloiu et al.

(10) Patent No.: US 8,827,943 B2
(45) Date of Patent: *Sep. 9, 2014

(54) CATHETER

(71) Applicant: University of Pittsburgh—Of the Commonwealth System of Higher Education, Pittsburgh, PA (US)

(72) Inventors: George Oliviu Angheloiu, Dubois, PA (US); John A. Kellum, Jr., Pittsburgh, PA (US); William D. Anderson, Pittsburgh, PA (US); Catalin Toma, Pittsburgh, PA (US)

(73) Assignee: University of Pittsburg—Of The Commonwealth System of Higher Education, Pittsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/804,989

(22) Filed: Mar. 14, 2013

(65) Prior Publication Data

US 2013/0197418 A1 Aug. 1, 2013

Related U.S. Application Data

(63) Continuation of application No. 12/061,562, filed on Apr. 2, 2008, now Pat. No. 8,398,576.

(60) Provisional application No. 60/921,680, filed on Apr. 2, 2007.

(51) Int. Cl.
*A61M 1/34* (2006.01)
*A61M 25/00* (2006.01)
*A61M 25/10* (2013.01)
*A61M 1/00* (2006.01)
*A61M 5/00* (2006.01)

(52) U.S. Cl.
CPC ............ *A61M 25/007* (2013.01); *A61M 1/008* (2013.01); *A61M 25/0021* (2013.01); *A61M 25/0041* (2013.01); *A61M 25/0054* (2013.01); *A61M 25/0068* (2013.01); *A61M 25/008* (2013.01); *A61M 5/007* (2013.01); *A61M 2202/0007* (2013.01); *A61M 2202/0014* (2013.01); *A61M 2202/0468* (2013.01)
USPC ....... 604/6.09; 604/5.01; 604/5.04; 604/6.16; 604/93.01

(58) Field of Classification Search
CPC ............ A61M 1/008; A61M 25/0021; A61M 25/0041; A61M 25/0054; A61M 25/0068; A61M 25/007; A61M 25/0071; A61M 25/008; A61M 25/0133; A61M 2025/0021; A61M 2025/0067; A61M 2025/0068; A61M 2025/0105; A61M 2202/0007; A61M 2202/001
USPC ......... 604/6.09, 4.01, 5.01, 5.04, 6.16, 93.01, 604/523, 96.01, 104, 105, 106
See application file for complete search history.

(56) References Cited

U.S. PATENT DOCUMENTS 4,643,716 A * 2/1987 Drach .............................. 604/8
4,681,570 A   7/1987 Dalton (Continued)

FOREIGN PATENT DOCUMENTS

EP    1 859 826 A1   11/2007
GB    2 349 825 A    11/2000

(Continued)

OTHER PUBLICATIONS

Ash et al., "Introduction: Sorbents in Extracorporeal Blood Therapy," *Advances in Renal Replacement Therapy*, 9(1): 1-2 (Jan. 2002).

(Continued)

*Primary Examiner* — Adam Marcetich
(74) *Attorney, Agent, or Firm* — Leydig, Voit & Mayer, Ltd.

(57) ABSTRACT

In one aspect, the invention provides a device comprising a catheter. In another aspect, the invention provides a method of removing an agent from blood.

19 Claims, 5 Drawing Sheets

(56) References Cited

U.S. PATENT DOCUMENTS

| | | | |
|---|---|---|---|
| 4,694,838 | A | 9/1987 | Wijayarthna et al. |
| 4,935,004 | A | 6/1990 | Cruz |
| 5,211,639 | A | 5/1993 | Wilk |
| 5,554,114 | A | 9/1996 | Wallace et al. |
| 5,709,874 | A | 1/1998 | Hanson et al. |
| 5,800,413 | A | 9/1998 | Swartz et al. |
| 5,846,223 | A | 12/1998 | Swartz et al. |
| 5,904,663 | A | 5/1999 | Braverman et al. |
| 6,053,900 | A | 4/2000 | Brown et al. |
| 6,074,378 | A | 6/2000 | Mouri et al. |
| 6,132,824 | A * | 10/2000 | Hamlin .................... 428/35.2 |
| 6,408,894 | B1 | 6/2002 | Davankov |
| 6,416,487 | B1 | 7/2002 | Braverman et al. |
| 6,442,415 | B1 * | 8/2002 | Bis et al. .................. 600/420 |
| 6,478,778 | B1 | 11/2002 | Jacobsen et al. |
| 6,527,735 | B1 | 3/2003 | Davankov et al. |
| 6,663,613 | B1 | 12/2003 | Evans et al. |
| 6,878,127 | B2 | 4/2005 | Brady et al. |
| 6,929,633 | B2 | 8/2005 | Evans et al. |
| 6,969,379 | B1 | 11/2005 | Aboul-Hosn et al. |
| 7,163,520 | B2 | 1/2007 | Bernard et al. |
| 7,276,043 | B2 | 10/2007 | Heath et al. |
| 7,312,023 | B2 | 12/2007 | Brady et al. |
| 7,363,072 | B2 | 4/2008 | Movahed |
| 8,398,576 | B2 | 3/2013 | Angheloiu et al. |
| 2001/0016725 | A1 | 8/2001 | Valley et al. |
| 2002/0087143 | A1 | 7/2002 | Forsberg |
| 2002/0091349 | A1 | 7/2002 | Reich |
| 2002/0099254 | A1 | 7/2002 | Movahed |
| 2003/0054037 | A1 | 3/2003 | Babcock et al. |
| 2003/0191448 | A1 | 10/2003 | Swindle |
| 2004/0044302 | A1 | 3/2004 | Bernard et al. |
| 2004/0147900 | A1 | 7/2004 | Polaschegg et al. |
| 2005/0145573 | A1 * | 7/2005 | Nanko et al. ............... 210/690 |
| 2005/0187467 | A1 * | 8/2005 | Kleen ....................... 600/433 |
| 2005/0209579 | A1 | 9/2005 | Yacoubian et al. |
| 2005/0239041 | A1 | 10/2005 | Brady et al. |
| 2005/0261663 | A1 * | 11/2005 | Patterson et al. ............ 604/508 |
| 2006/0057142 | A1 | 3/2006 | Brady et al. |
| 2006/0229705 | A1 | 10/2006 | Deal |
| 2006/0253101 | A1 | 11/2006 | Hartlep et al. |
| 2007/0060908 | A1 * | 3/2007 | Webster et al. ............. 604/509 |
| 2007/0225661 | A1 * | 9/2007 | Ash et al. .................. 604/284 |
| 2007/0243267 | A1 | 10/2007 | Barnett et al. |
| 2007/0292429 | A1 | 12/2007 | Brady et al. |
| 2008/0108960 | A1 | 5/2008 | Shapland et al. |
| 2008/0138434 | A1 | 6/2008 | Brady et al. |
| 2008/0281248 | A1 | 11/2008 | Angheloiu et al. |
| 2009/0030362 | A1 * | 1/2009 | Michishita et al. .......... 604/6.11 |
| 2009/0182287 | A1 | 7/2009 | Kassab |

FOREIGN PATENT DOCUMENTS

| | | |
|---|---|---|
| WO | WO 00/62836 A2 | 10/2000 |
| WO | WO 00/62836 A3 | 10/2000 |
| WO | WO 00/62836 C2 | 10/2000 |
| WO | WO 03/057306 A1 | 7/2003 |
| WO | WO 03/057308 A2 | 7/2003 |
| WO | WO 03/057308 A3 | 7/2003 |
| WO | WO 03/057308 C1 | 7/2003 |
| WO | WO 03/057309 A2 | 7/2003 |
| WO | WO 03/057309 A3 | 7/2003 |
| WO | WO 03/057356 A2 | 7/2003 |
| WO | WO 03/057356 A3 | 7/2003 |
| WO | WO 03/063942 A1 | 8/2003 |
| WO | WO 03/103472 A2 | 12/2003 |
| WO | WO 03/103472 A3 | 12/2003 |
| WO | WO 2006/090706 A1 | 8/2006 |

OTHER PUBLICATIONS

Cruz et al., "Extracorporeal Blood Purification Therapies for Prevention of Radiocontrast-Induced Nephropathy: A Systematic Review," *American Journal of Kidney Diseases*, 48(3): 361-371 (Sep. 2006).

Department of Physico-Chemical Mechanisms of Adsorptive Detoxification, 1-2 (Jan. 3, 2004) [www.onconet.kiev.ua/iepor/adsorbents.html].

Frank, "Simultaneous hemodialysis during coronary angiography fails to prevent radiocontrast-induced nephropathy in chronic renal failure," *Clinical Nephrology.* 60(3): 176-182 (Sep. 2003).

Gleeson et al., "Contrast-Induced Nephropathy," *American Journal of Roentgenology*, 183: 1673-1689 (Dec. 2004).

Kohler et al., "Dialysis access failure: A sheep model of rapid stenosis," *Journal of Vascular Surgery*, 30(4): 744-751 (Oct. 1999).

Mallery et al., "Assessment of normal and atherosclerotic arterial wall thickness with an intravascular ultrasound imaging catheter," *American Heart Journal*, 119(6): 1392-1400 (Jun. 1990).

Meyer et al., "Coronary Venous Capture of Contrast during Angiography," *Journal of Interventional Cardiology*, 19(5): 401-404 (2006).

Michishita et al., "A Novel Contrast Removal System From the Coronary Sinus Using an Adsorbing Column During Coronary Angiography in a Porcine Model," *Journal of the American College of Cardiology*, 47(9): 1866-1870 (May 2, 2006).

Movahed et al., "Removal of Iodine Contrast From Coronary Sinus in Swine During Coronary Angiography," *Journal of the American College of Cardiology*, 47(2): 465-467 (Jan. 17, 2006).

Nash et al., "Hospital-Acquired Renal Insufficiency," *American Journal of Kidney Disease*, 39(5): 930-936 (May 2002).

Schindler et al., "Removal of contrast media by different extracorporeal treatments," *Nephrology Dialysis Transplantation*, 16(7): 1471-1474 (Jul. 2001).

United States Patent and Trademark Office, International Search Report dated Dec. 4, 2009, in PCT/US2009/59426.

Watanabe et al., "Efficacy of Bacteriophage Therapy against Gut-Derived Sepsis Caused by *Pseudomonas aeruginosa* in Mice," *Antimicrobial Agents and Chemotherapy*, 51(2): 446-452 (Feb. 2007).

U.S. Appl. No. 12/061,562, filed Apr. 2, 2008.

Chang et al., "A Novel Technique for Endovascular Detection and Removal of Radiographic Contrast during Angiography," *The Journal of Invasive Cardiology*, 21(7): 314-318 (Jul. 2009).

* cited by examiner

CATHETER

CROSS-REFERENCE TO RELATED APPLICATIONS

This application is a continuation of co-pending U.S. patent application Ser. No. 12/061,562, which was filed on Apr. 2, 2008, and which claims priority to U.S. Provisional Patent Application 60/921,680, filed Apr. 2, 2007. The contents of these prior applications are incorporated herein in their entirety.

STATEMENT REGARDING FEDERALLY SPONSORED RESEARCH AND DEVELOPMENT

This invention was made in part with Government support under Grant Numbers 5R01HL080926 awarded by the United States National Institutes of Health. The Government has certain rights in this invention.

BACKGROUND OF THE INVENTION

Advances in medical diagnostic imaging have greatly increased the utility of many radiographic and cardiologic procedures it is expected that greater numbers of patients will undergo these procedures in the years to come. Unfortunately, these procedures continue to rely on iodinated contrast (such as Iopamiron 370, iodixanol, etc.) for identification of vascular structures and no viable alternatives have yet emerged. For example, such agents are often injected in the brain arteries during brain arterial procedures.

While advances have been made in the design and composition of contrast, these agents still carry a risk of renal injury and account for a significant number of cases of hospital-acquired renal failure (Gleeson and Bulugahapitiya Am J Roentgenol 2004; 183:1673-1689; Nash et al. Am J Kidney Dis 2002; 39:930-936.). Contrast-induced nephropathy (CIN), defined as evidence of renal injury or dysfunction following exposure to contrast agents for imaging studies is a common and potentially serious complication. The risk of CIN is highest in patients with underlying kidney disease or injury, but multiple other risk factors have been identified including intra-arterial administration of contrast, higher contrast volumes (>100 mL), diabetes and underlying cardiac disease. CIN has an incidence of 15% of cases performed in the brain vasculature, and it carries a mortality risk of 0.8-1%.

No adjunctive medical or mechanical treatment has been proved to be efficacious in reducing the risk of CIN. In principal, removal of contrast directly from whole blood could significantly reduce the risk of CIN particularly if it could be done rapidly and with higher efficiency, before significant exposure to the kidneys could take place. However, current clinical techniques to prevent nephropathy are only medical and are notoriously inefficacious. For example, U.S. Patent Application Publication No. 2002-0099254 (Movahed et al.) proposes a method to remove contrast agent from vessels of the heart that involves filtration using a membrane that catches everything but red blood cells, centrifugation to remove red blood cells, or suctioning off portions of the patient's blood. However, late application of such limited efficacy blood purification, such as using traditional hemodialysis is ineffective (Frank Clin Nephrol 2003:60; 176-182). Accordingly, more effective technologies for minimizing the risk of contrast-induced nephropathy are desirable.

BRIEF SUMMARY OF THE INVENTION

The invention provides a system and a method for removal of contrast from blood. In one aspect, the invention provides a catheter for removal of blood from the veins that drain the cerebral circulation. The present catheter in this or modified configuration could drain blood from other venous systems, including but not limited to the venous systems of the heart, upper extremities and lower extremities, kidney and liver. In a second aspect, the invention provides a method for removing contrast from blood by contacting the blood with a sorbent. These aspects and additional inventive features will be apparent from the accompanying drawings and the following brief description.

DETAILED DESCRIPTION OF THE INVENTION

Figure 4:
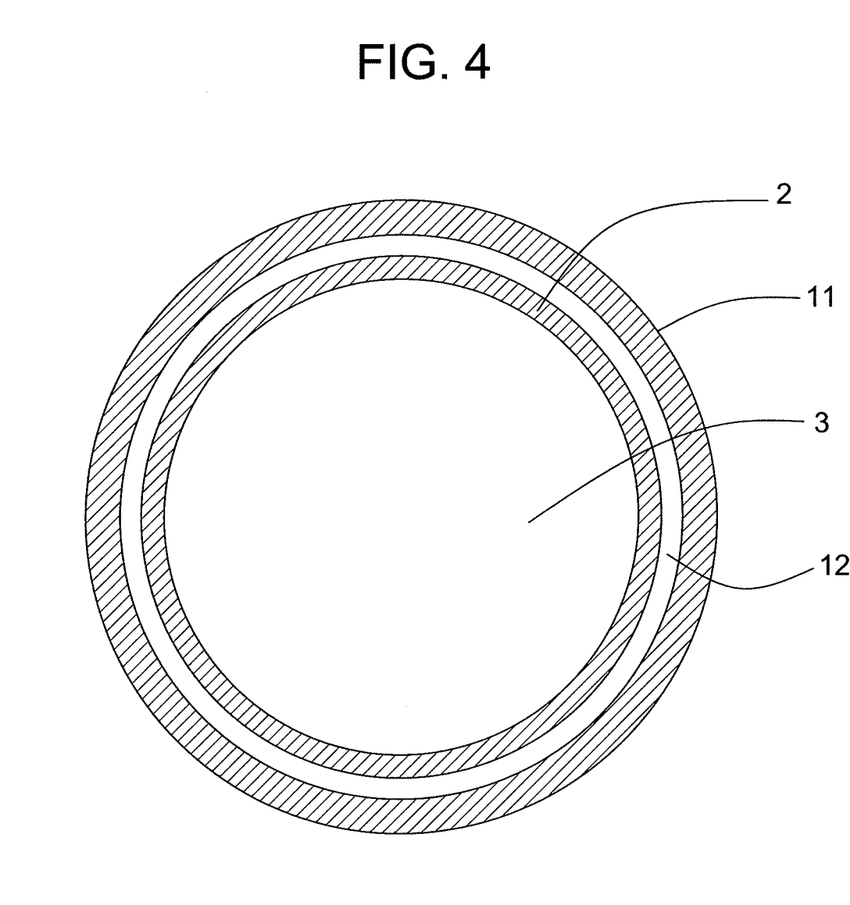
FIG. 4 is a cross section of the inner and optional outer catheters of the inventive catheter system.

With reference to FIGS. 1-4, the inventive system for removing blood from the venous system that drains the cerebral circulation can comprise central catheter 1 comprising an inner wall 2 and an inner lumen 3 (FIG. 4). Central catheter 1 comprises a proximal portion 4 of the system, which has a tip 5 and at least one lateral fenestration 6 in fluid connection with the lumen 3 of the central catheter 1. The fenestration 6 is laterally disposed in the wall of the proximal portion 4 of the central catheter 1 to facilitate the drainage of blood from the patient through the fenestration 6 and through the lumen 3 of the central catheter 1. Typically, the proximal portion 4 has a plurality of fenestrations 6, although for placement in the SVC, the proximal portion 4 typically has fewer fenestrations 6 than catheters suitable for placement in the jugular. Lateral positioning of the fenestrations 6 assists in minimizing collapse of the walls of a patient's blood vessels upon application of suction. Of course, the tip 5 of the central catheter 1 can include an end fenestration 7 in fluid connection with the lumen 3 of the central catheter 1, which also facilitates drainage of the patient's blood through the catheter.

For placement in the jugular, preferably the proximal portion 4 has one or more curves 8, and preferably at least two curves 8a and 8b (see FIG. 2) somewhat in the shape of the letter "S." This configuration facilitates insertion into the jugular and enhances the stability of placement. Also, this configuration assists in minimizing collapse of the walls of a patient's blood vessels upon application of suction. Furthermore, in this embodiment, it is preferred for the lateral fenestrations 6 to be disposed on the concave sides of the curves 8, so that they are away from the walls of the patient's blood vessel into which the system is placed, which further assists in minimizing collapse of the walls of a patient's blood vessels upon application of suction.

In certain embodiments, the inventive catheter system can employ a balloon 9 to assist in occlusion of the patient's vessels. In such embodiments, the proximal portion 4 of the central catheter 1 optionally comprises an inflatable balloon 9 disposed distally from the side fenestration(s) 6. The balloon 9 can define the distal end of the proximal portion 4. Where present, the balloon 9 is positioned a suitable distance distal from the tip 5 (such as about 1, 2, 3, 4, 5, 6, 7, 8, 9, 0, 11, 12 13, 14, or 15 cm) to facilitate placement of the tip 5 in the desired location (e.g., within the superior vena cava (SVC) or jugular).

For placement of the tip 5 within the jugular, typically the balloon 9 is positioned about 10 cm to about 15 cm distal to the tip, in a way that the balloon 9 and at least one side fenestration 6 sit in the SVC. For placement of the tip 5 within the SVC, typically the balloon 9 is positioned about 1 cm to about 3 cm (e.g., about 2 cm) distal to the tip 5.

Where the inventive catheter system employs a balloon, 9, an outer catheter 10 comprising an outer wall 11 and an outer lumen 12 (FIG. 4) is coaxially disposed about the central catheter 1 and in fluid connection with the balloon 9. Thus, fluid (such as air or a suitable gas) can be introduced into the outer lumen 12 to as to inflate the balloon 9. Thus, the outer catheter 10 can be in fluid connection with a pump, syringe, or other similar device 19 for moving fluids into and out of catheters and balloons. In this embodiment, it will be observed (FIG. 4) that the wall 2 of the central catheter 1 is disposed within the outer lumen 12 of the outer catheter 10.

The shaft 13 of the central catheter 1 (and, when present, outer catheter 10) can be of a suitable length to facilitate placement within the patient. Preferably, the shafts 13 have a curved shape with the double purpose of stabilizing the catheter inside the central venous system for longer periods of time, and also for allowing an easier approach of the jugular veins. For the latter scope, the concave curvature of the shaft should face the particular side of the body with the same orientation as the jugular that is to be cannulated.

Figure 1:
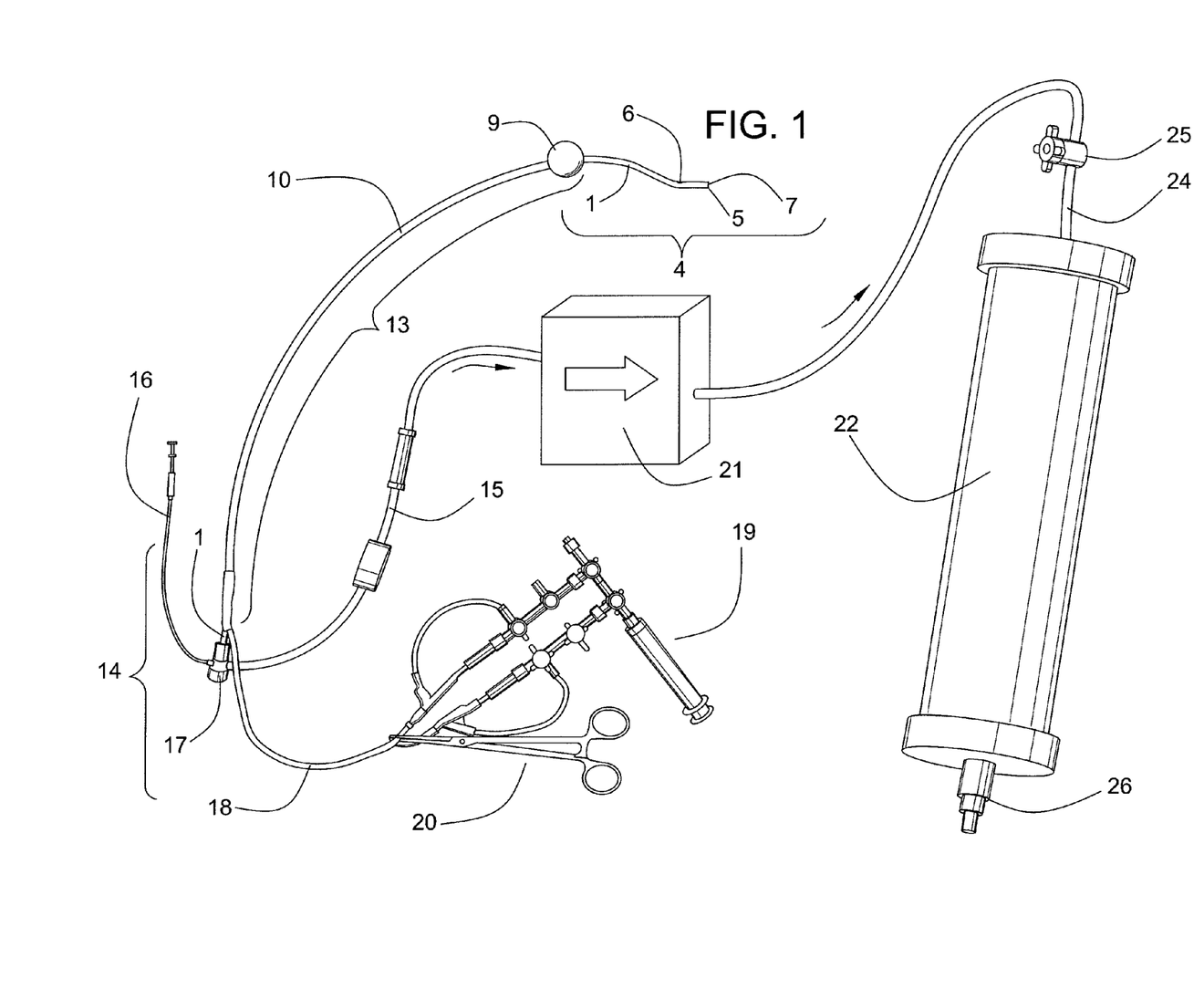
FIG. 1 depicts the inventive catheter system designed for jugular placement showing the optional balloon in the inflated position.
Figure 2:
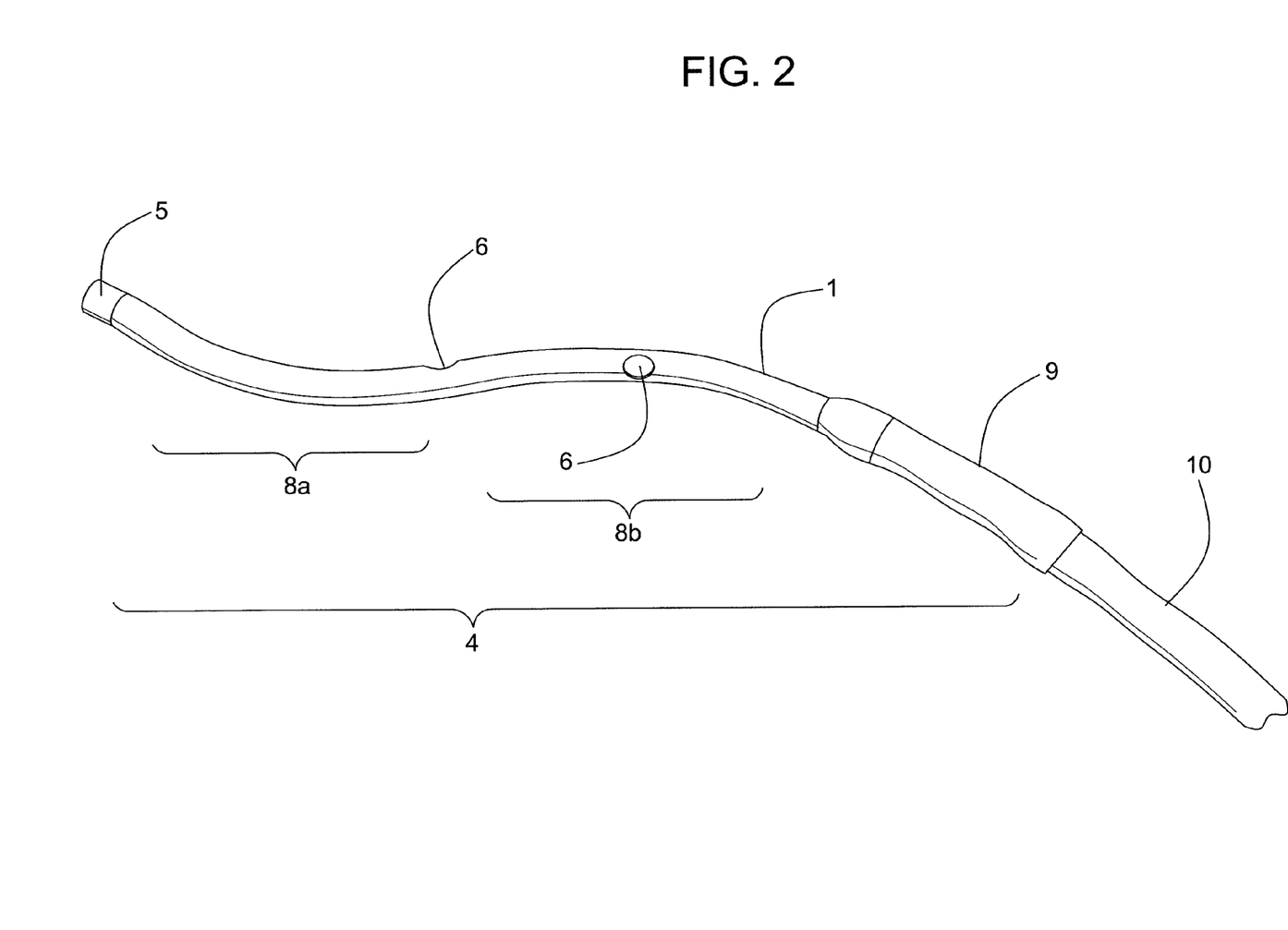
FIG. 2 depicts the detail of the inventive catheter system designed for jugular placement showing the optional balloon in the deflated position.
Figure 3:
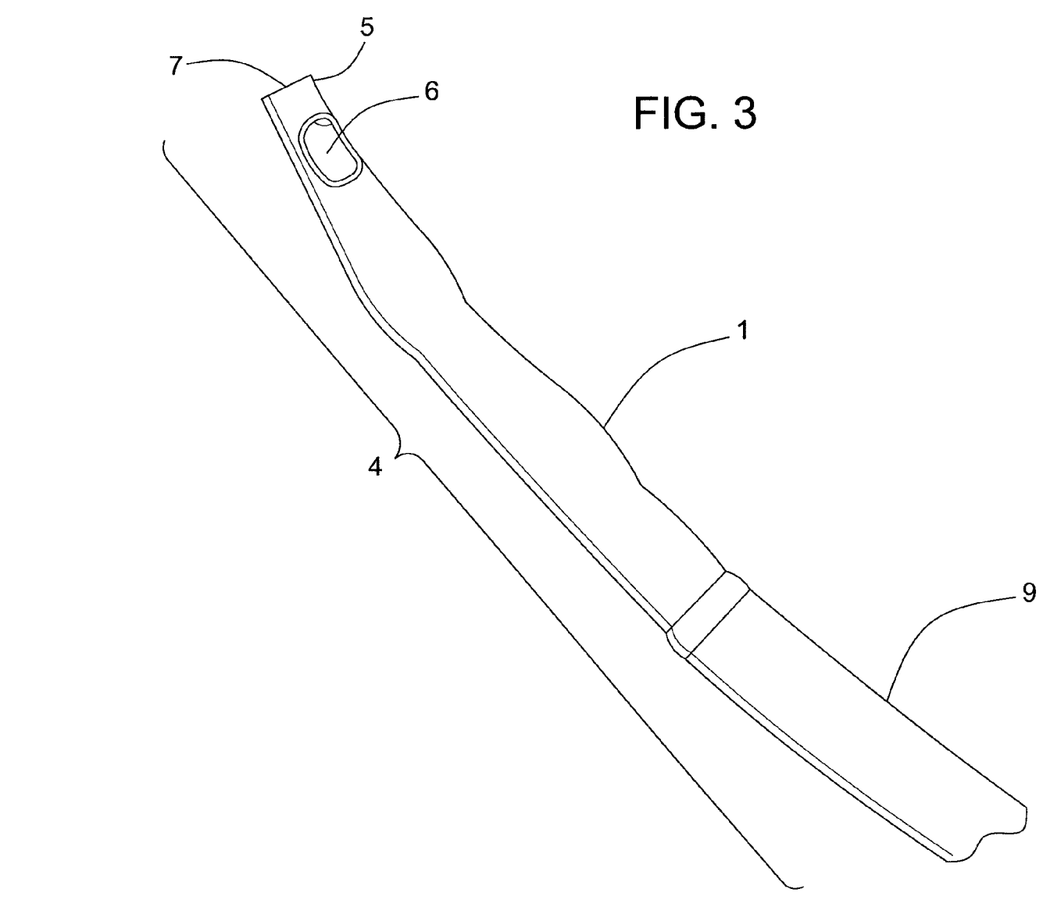
FIG. 3 depicts the detail of the inventive catheter system designed for SVC placement showing the balloon in the deflated position.

The inventive catheter system also includes a distal portion 14, which includes port(s) for the catheter(s). In FIG. 1, for example, there is depicted a first distal port 15 in fluid connection with the central catheter 1. It will be understood that fluid connectivity refers to connectivity with the lumen of a catheter. The first distal port 15 is in fluid connection to a suctioning device 21 (such as a vacuum container or a pump), which facilitates removal of blood from the patient through the lumen of the central catheter 1. The diameter of the distal port 15 desirably is approximately the same as the lumen 3 of the central catheter 1, so as to facilitate suction throughout the fluid connection. Furthermore, desirably, the suction device 21 also is in fluid connection with a medium suitable for removing contrast from the blood. Such a medium can be a membrane, column, filter, or other device that can be employed for removing contrast from blood. Desirably, the medium is a sorbent, which can be encased within a chamber 22 (FIGS. 1 and 5) as described herein.

FIG. 1 also depicts an injection port 16 in fluid connection with the central catheter 1, which can be employed to inject saline or other fluids (e.g., containing heparin or other desired agents) into the lumen of the central catheter. The injection port 16 is optional, and where present, its fluid connectivity to the central catheter and the first port can be controlled with a valve 17 or an occlusive device, such as a clamp.

For embodiments including the balloon 9, the distal portion 14 of the catheter system further includes a second distal port 18 for the outer catheter 10, which (via the lumen of the outer catheter) is in fluid communication with the balloon 9. The second distal port 18 is further in fluid connection with an inflation/deflation device 19 for applying positive and negative pressure to the outer catheter 10, which facilitates inflation and deflation of the balloon 9. While in FIG. 1, one typical such inflation/deflation device 19 is depicted, any other suitable inflation/deflation device for controlling balloon catheters can be alternatively employed. Furthermore, the fluid connectivity between the inflation/deflation device 19 and the second distal port 18 can be controlled with a clamp 20 (as depicted), valve, or other similar mechanism.

It will be observed that the catheter system can be manufactured using standard materials suitable for use in patients. Moreover, the components of the catheter system can be fabricated by standard methods known to those of ordinary skill.

Desirably, the catheter system is suitable for insertion into a patient through the groin/femoral vein and also for positioning the tip 5 within a patient's SVC or jugular such that the balloon 9, when present, occludes said SVC when inflated. Accordingly, preferably, the central catheter 1 is an 11 F catheter. In this configuration, the outer catheter 10 is a 12 F or a 13 F catheter to facilitate coaxial disposition about the central catheter 1. Moreover, preferably, the balloon 9 can inflate to about 3 cm in diameter when fully inflated, as this facilitates sealing the patient's circulatory system distal to the balloon 9 from the tip 5.

When inserted through the groin/femoral vein, the length of the catheter system from the distal portion 14 to the tip 5 can be adjusted by the physician depending on the size and anatomy of the patient. However, typically, the system is about 60 cm from the distal portion 14 to the tip 5. Also, the catheters desirably comprise a slight curvature at the connection between the distal third with the proximal two thirds, in order to better accommodate the junction between the femoral-iliac system and the inferior vena cava.

In one preferred embodiment, a catheter suitable for insertion into the jugular has the following dimensions:
  upper portion of "S" curve of the end portion (4): 5 cm, with fenestrations (6) opening towards the concave side of the catheter end portion (4) shaft,
  lower portion of "S" curve of the end portion (4): 5, cm, with fenestrations (6) opening towards the concave side of the catheter end portion (4) shaft,
  balloon (9) length: 4 cm,
  diameter of balloon (9) when inflated: 3 cm,
  shaft length to balloon (9): 42 cm,
  length of distal port outlets: 9 cm, and
  external diameter of the shaft: 5 mm.

In operation, the tip 5 of the central catheter 1 is inserted into a suitable blood vessel of a patient, preferably into the femoral vein. Thereafter, the central catheter 1 (and, when present, the coaxially-disposed outer catheter 10) is inserted deeper into the patient's circulatory system, passing through the inferior vena cava and right atrium into the SVC, until the balloon 9 (if present) is positioned in the SVC. In this position, the proximal tip 5 will be placed 3-4 cm above the junction between the right atrium and SVC (for SVC placement) or within the jugular, depending on the type of catheter. In this position, the balloon 9 (if present) can be inflated to occlude the SVC. In this position, the suction device 21 is engaged to achieve high flow suctioning of blood from the patient through the lateral fenestration(s) 6 (and, if present, end fenestration 7) and, hence, through the lumen 3 of the inner catheter 1 and out of the patient. Desirably, the suctioning occurs at a rate of about 600-1000 cc/min.

The operator will suction blood (which can contain contrast) from the SVC (which drains blood from brain and upper limbs) for a few seconds (e.g., about 4 seconds, which is the transit time between cerebral arteries and veins that has been calculated based on current angiographic techniques) after injecting blood, contrast, or other material into the carotid artery or the cerebral artery to be intervened upon. For jugular placements, intense suctioning from the jugular vein on the side of intervention (i.e., contrast introduction) is achieved. Typically, the operation of the inventive catheter system can achieve removal of at least about 80% (such as at least about 85% or at least about 90%) of the blood from the venous system returning blood from cerebral circulation.

Contrast flows with predilection in the jugular vein on the side of the intervention. Thus, when the system is employed for drainage of blood to remove contrast, by placing more lateral fenestrations 6 in that area of the catheter, the bulk of the contrast is captured, because the vacuum will direct blood flow and hence the contrast to that side of the jugular system. Also, preferably, the balloon 9 (where present) is inflated in the SVC, so even contrast from the other jugular, although typically much less, also is suctioned. It is noted that a balloon is optional. However, where a balloon 9 is employed, while suctioning blood and contrast from the vein, the balloon 9 can be inflated within the SVC to prevent contrast from leaking into the right atrium. This mechanically removes the contrast before it enter the systemic circulation, and hence reaches the kidney.

The blood and contrast then is filtered, typically by passing the blood+contrast through an extracorporeal device 22, to remove the contrast from the blood, whereupon the blood is reinjected back into the venous circulation of the patient. The direction of blood flow from the catheter system, through the suction device 21 and through the extracorporeal device 22 is indicated generally by arrows in FIGS. 1 and 5. Following the procedure, the catheter system is removed from the patient, and the patient is sutured and otherwise treated for post-operative recovery.

In another aspect, the invention provides a method of removing contrast from blood. The method comprises circulating blood containing contrast through a sorbent, and returning the effluent blood from the sorbent to the patient. Desirably, the method comprises first removing blood containing contrast from the patient and circulating the blood extracorporeally through the sorbent to remove the contrast. However, in some embodiments, the sorbent can be employed intracorporeally (e.g., within a catheter or within a mesh or porous chamber within a patient).

Preferably the method is employed using whole blood, rather than plasma or other fractionated blood product. This minimizes processing of the patient's blood and facilitates return of all or nearly all components of the patient's blood after processing to remove the contrast.

In preferred embodiments, the blood+contrast can be withdrawn from the patient following cerebral intervention employing the inventive catheter system as described above. However, it will be understood that the sorbent can be used to remove the contrast from blood withdrawn from any location in the patient (including but not limited to heart, kidney liver, upper and lower extremities), during any type of medical tests (such as cardiac or radiologic diagnostic tests or interventions), or using any type of contrast material.

A number of suitable sorbents are available, including polymers and activated carbon. While any sorbent system can be used in the context of the inventive method, preferably the sorbent system is polymeric. Preferred sorbents for use in the inventive method include Sorbents with high surface area (high capacity) and high adsorptive properties can be used and are currently in use to remove certain harmful plasma proteins such as antibodies. One suitable sorbent system for use in the inventive method the CytoSorb polymer manufactured by MedaSorb Technologies, Princeton N.J. Another suitable sorbent that can be used in the inventive method comprises carbonic pyropolymers (Hemoadsorbents Granular Deliganding—"HSGD"), which is manufactured in the Ukraine (manufactured in the Ukraine (www.onconet.kiev.ua/iepor/adsorbents.html). The CytoSorb polymer is a hydrated, porous adsorbent bead that was developed to target plasma proteins in range in size from 8 to 40 kilodaltons. Additional information concerning suitable sorbents is discussed in several patent documents (see, e.g., European Patent Application Publications 1 115 456 A2 and 1 463 548, U.S. Patent Application Publications 2005-0239041 A1, 2006-0057142 A1, and 2007-0292429 A1, U.S. Pat. Nos. 6,408,894, 6,527,735, 6,878,127, and 7,312,023, and International Patent Application Publications WO/2000/062836, WO/2003/057306, WO/2003/057308, WO/2003/057309, WO/2003/057356, and WO/2003/103472, which are incorporated herein by reference).

Figure 5:
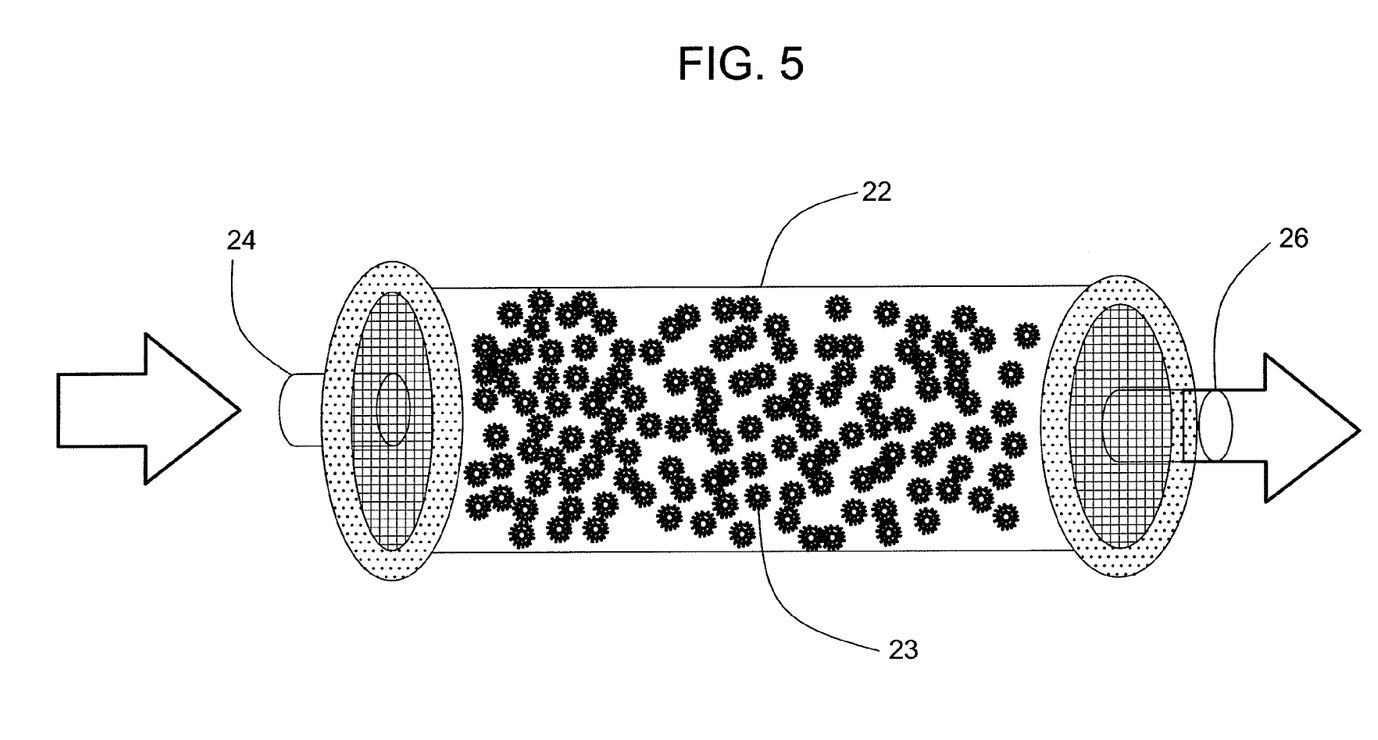
FIG. 5 schematically illustrates the sorbent chamber for use in the inventive method.

Typically, the sorbent is fabricated as small beads, which can be retained within the chamber 22. However, other forms of sorbent (e.g., microtubular, nanotubular, microparticles, etc.) can be similarly employed. The pores on the surface of the polymer are engineered to permit the entry of molecules in this size range (e.g., the size range of contrast), but exclude larger, important proteins, such as albumin and immunoglobulins. Once inside the interior of the bead or other particle, the molecules adsorb to the inner surface of the bead or other particle. Sorbent polymer beads typically range in size from 425 to 1000 microns and each gram of beads has over 850 square meters of surface area available for adsorption. HSGD carbon has beads with very high available surface. HSGD has been used for therapeutic aphaeresis directly from blood the Ukraine for several years. Other sorbents also can be used.

For use in the inventive method, the sorbent is contained within a chamber 22 that retains the sorbent material while permitting the flow of blood past and through the sorbent. The chamber 22 can be, for example, a section of tubing or a mesh or porous sac (which can enable use in vivo). However, typically, the chamber 22 is a column and is used extracorporeally. Turning to FIG. 5, there is depicted a suitable sorbent chamber 22 comprising polymeric sorbent beads 23. The chamber 22 can be attached to influent 24 (inflow of blood+contrast from the patient) and effluent 26 (outflow of blood cleansed of contrast to the patient) conduits. As depicted in FIG. 1, a valve 25 can optionally be employed to control the rate of flow of blood+contrast into the chamber 22.

Without wishing to be bound by theory, it is believed that the sorbent uses aphaeresis to remove contrast from blood. Aphaeresis is a technique whereby molecules are removed directly from the blood without a blood separation process such as filtration or dialysis. In accordance with the inventive method, blood is pumped or otherwise introduced into the chamber 22 containing the sorbent and then returned to the patient in a closed loop. In this application, contrast is removed by the sorbent and blood returning to the patient has been depleted of contrast without significant other changes.

Using the sorbent system, greater than about 75% of the contrast can be removed from the blood passing through the sorbent chamber, and the results presented in the example, reveal that greater than about 80%, such as greater than about 85%, greater than about 90%, greater than about 95%, and even greater than 99% of the contrast can be removed from the blood treated with the sorbent. Depending on the manner in which the blood+contrast is removed from the patient, greater than 50% of the contrast can be removed from the patient, and in some embodiments, greater than about 60%, such as greater than about 70% or greater than about 75% of the contrast can be removed from the patient. More preferably, the inventive method removes greater than about 80%, such as greater than about 85% or greater than about 90% or even greater than about 95% of the contrast from the patient.

It will be understood that a "patient" to be treated in the context of the present invention can be a human patient. However, the inventive system for removing blood+contrast in conjunction with cerebral intervention, and the method for removing contrast from blood, can be applied in the context of veterinary procedures (e.g., the patient can be a household pet, such as a cat or a dog, or an agriculturally-important animal, such as a pig, goat, cow, horse, etc). Also, the method and catheter system have application in the laboratory context, and can be employed in animal systems commonly employed in biomedical research (e.g., pigs, dogs, monkeys, apes, etc.).

Within the context of the invention, the "contrast" can be any contrast suitable for diagnostic medical imaging. However, the inventive method and catheter system is well suited to removing iodinated media such as iopamiron 370, iodixanol, etc.

EXAMPLE 1

This example demonstrates the use of a sorbent for removing contrast from blood. This example further illustrates the invention but, of course, should not be construed as in any way limiting its scope.

A cartridge containing 500 gm CytoSorb beads (MedaSorb Technologies, Princeton N.J.) is flushed with saline. 900 ml of blood was reconstituted from 675 ml of packed red blood cells and 225 ml of normal saline. 45 ml of iodixanol (Visipaque, GE), containing a total of 14400 mg of iodine (320 mg/ml) is mixed with the 900 ml of blood. 600 ml of the blood and contrast mixture is separated in 12 samples of 50 ml each. 6 samples is passed through a device at a rate of 60 ml/min. Another 6 samples were left untreated as controls. Plasma is separated in all 12 specimens, and then subjected to X-ray fluorescence spectrometry for iodine concentration measurement. The resulting concentrations with changes and percent changes are provided in table 1 below. Greater than 99.8% of the contrast is removed after a single pass through the device.

TABLE 1

| Control | Treatment | % Reduction |
| --- | --- | --- |
| 20916 | 9 | 99.86% |
| 21552 | 11 | 99.89% |
| 20616 | 6 | 99.92% |
| 21501 | 10 | 99.89% |
| 20894 | 11 | 99.87% |
| 19906 | 9 | 99.82% | iodine concentrations are expressed in μg/ml

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A device comprising:
   (a) catheter (1) comprising a wall (2) and a lumen (3) and comprising
      (i) proximal portion (4), said proximal portion (4) having, a tip (5) and a plurality of lateral fenestrations (6) in fluid connection with the lumen (3) of said catheter (1), and in which said proximal portion (4) comprises at least two curves (8a) and (8b) in substantially planar arrangement, and in which each of said lateral fenestrations (6) is disposed at the concave side of curves (8a) and (8b), and wherein the placement of the lateral fenestrations (6) is adapted to minimize collapse of the walls of a patient's blood vessels upon application of suction, and
      (ii) distal portion (14) comprising a distal port (15) in fluid connection with said catheter (1).

2. The device of claim 1, wherein said tip (5) comprises an end fenestration (7) in fluid connection with the lumen(3) of said catheter (1).

3. The device of claim 1, wherein said catheter (1) comprises a slight curvature at the connection between the distal third with the proximal two thirds to accommodate the junction between femoral-iliac system and the inferior vena cava.

4. The device of claim 3, wherein said catheter (1) comprises a curve suitable to stabilize the catheter (1) within the central venous system and to facilitate approach to the jugular veins.

5. The device of claim 1, which is suitable far placement of said tip (5) into the superior vena cava (SVC) of a human patient for removing blood from said SVC.

6. The device of claim 1, which is suitable for placement of said tip (5) into the jugular vein of a human patient for removing is from said jugular vein.

7. The device of claim 1, wherein said catheter (1) is suitable for insertion into a patient through the groin femoral artery.

8. The device of claim 1, wherein the diameter of said distal port (15) is approximately the same as the lumen (3) of said catheter (1).

9. The device of claim 1, comprising inflatable balloon (9) disposed distally from said lateral fenestrations (6), said device further comprising:
   (b) outer catheter (10) comprising outer wall (11) and outer lumen (12), coaxially disposed about said catheter (1) and in fluid connection with said balloon (9), and second distal port (18) in fluid connection with said outer catheter (10).

10. The device of claim 1 or 9, which comprises two curves (8a) and (8b).

11. The device of claim 10 in which said curves (8a) and (8b) are arranged consecutively as in the manner of the letter "S."

12. The device of claim 1 or 9, in which said curves (8a) and (8b) are arranged consecutively as in the manner of the letter "S."

13. The device of claim 1 or 9, comprising a suction device (21) in fluid connection with said distal port (15).

14. The device of claim 13, comprising a sorbent chamber (22) in fluid connection with said catheter (1) and said suction device (21), wherein said sorbent chamber (22) comprises sorbent.

15. A method of removing an agent from blood, said method comprising:
   (a) inserting, the device of claim 13 into a patient so that said tip (5) is located within a vein;
   (b) infecting an agent into an artery of the patient, wherein there exists a fluid transit time between the site of said injection and the location of said tip (5), and
   (c) removing blood containing, the agent from the patiet using said suction device (21).

16. The method of claim 15, wherein the blood containing said agent is removed in (c) after a period of time approximating said fluid transit time.

17. The method of claim 16, further comprising circulating, the blood containing the agent through sorbent, removing the effluent blood from the sorbent, and reintroducing the effluent blood to the patient.

18. The method of claim 17, which removes greater than 95% of the agent from the blood prior to returning the blood to the patient.

19. The method of claim 15, wherein said is contrast agent.

* * * * *

UNITED STATES PATENT AND TRADEMARK OFFICE
CERTIFICATE OF CORRECTION

PATENT NO. : 8,827,943 B2
APPLICATION NO. : 13/804989
DATED : September 9, 2014
INVENTOR(S) : Angheloiu et al.

It is certified that error appears in the above-identified patent and that said Letters Patent is hereby corrected as shown below:

On the title page, item (73) Assignee: replace "University of Pittsburg – Of The Commonwealth System of Higher Education, Pittsburg, PA (US)" with --University of Pittsburgh – Of the Commonwealth System of Higher Education, Pittsburgh, PA (US)--

In the Claims

In Column 8, line 56: replace "5. The device of claim 1, which is suitable far placement of" with --5. The device of claim 1, which is suitable for placement of--

In Column 8, lines 60-61: replace "said tip (5) into the jugular vein of a human patient for removing is from said jugular vein." with --said tip (5) into the jugular vein of a human patient for removing blood from said jugular vein.--

In Column 8, line 63: replace "able for insertion into a patient through the groin femoral" with --able for insertion into a patient through the groin/femoral--

In Column 10, line 3: replace "inserting, the device of claim 13 into a patient so that" with --inserting the device of claim 13 into a patient so that--

In Column 10, line 5: replace "(b) infecting an agent into an artery of the patient, wherein" with --(b) injecting an agent into an artery of the patient, wherein--

In Column 10, line 8: replace "(c) removing blood containing, the agent from the patiet" with --(c) removing blood containing the agent from the patient--

In Column 10, lines 13-14: replace "17. The method of claim 16, further comprising circulating, the blood containing the agent through sorbent, removing" with --17. The method of claim 16, further comprising circulating the blood containing the agent through sorbent, removing--

Signed and Sealed this
Fifth Day of May, 2015

Michelle K. Lee
*Director of the United States Patent and Trademark Office*

In Column 10, line 20: replace "19. The method of claim 15, wherein said is contrast agent." with
--19. The method of claim 15, wherein said agent is contrast agent.--